US008184886B2

(12) United States Patent
Khamene et al.

(10) Patent No.: US 8,184,886 B2
(45) Date of Patent: May 22, 2012

(54) DEFORMABLE 2D-3D REGISTRATION

(75) Inventors: Ali Khamene, Princeton, NJ (US); Oliver Fluck, Plainsboro, NJ (US); Shmuel Aharon, West Windsor, NJ (US)

(73) Assignee: Siemens Aktiengesellschaft, München (DE)

(*) Notice: Subject to any disclaimer, the term of this patent is extended or adjusted under 35 U.S.C. 154(b) by 950 days.

(21) Appl. No.: 12/192,278

(22) Filed: Aug. 15, 2008

(65) Prior Publication Data

US 2009/0052757 A1 Feb. 26, 2009

Related U.S. Application Data

(60) Provisional application No. 60/957,016, filed on Aug. 21, 2007.

(51) Int. Cl.
*G06K 9/00* (2006.01)

(52) U.S. Cl. ........................................ 382/131; 382/294

(58) Field of Classification Search .................. 382/107, 382/128, 131, 132, 154, 294
See application file for complete search history.

(56) References Cited

U.S. PATENT DOCUMENTS 5,633,951 A * 5/1997 Moshfeghi .................... 382/154
2006/0274061 A1* 12/2006 Wang et al. .................. 345/420
2008/0080788 A1* 4/2008 Nord et al. .................... 382/294

* cited by examiner

*Primary Examiner* — Andrew W Johns
(74) *Attorney, Agent, or Firm* — Donald B. Paschburg

(57) ABSTRACT

A method for deformable registration including determining a vector field from a two-dimensional matching of a volume of an object of interest and a two-dimensional image of the object of interest, providing a deformation profile, and finding a volume deformation that maps to a state of the two-dimensional image, wherein the deformation is parameterized by the vector field and control points of the deformation profile to find a control point configuration of the volume deformation.

12 Claims, 5 Drawing Sheets

601 DETERMINE VECTOR FIELD FROM 2D MATCHING OF SIMULATED 2D IMAGE AND ACTUAL 2D IMAGE OF AN OBJECT OF INTEREST

602 MAP THE 2D VECTOR FIELD TO A 3D GRID TO SCALE TRANSLATIONS OF CONTROL POINTS IN 3D

603 PROVIDING DEFORMATION PROFILE OF THE OBJECT OF INTEREST

604 DETERMINE TRANSLATION DIRECTIONS OF CONTROL POINTS IN 3D

605 UPDATING A VOLUME DEFORMATION ACCORDING TO THE VECTOR FIELD AND THE DEFORMATION PROFILE

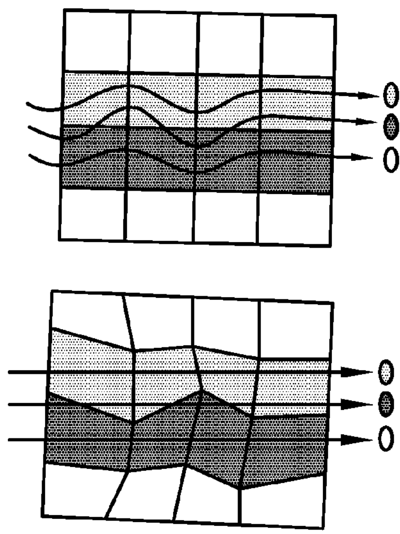
FIG. 2A
FIG. 2B
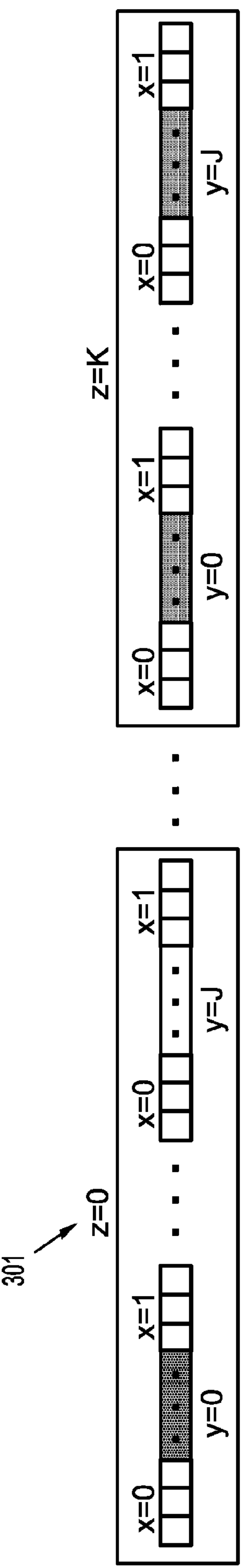
FIG. 3A
Ctrl point (0,0,0)
301
Ctrl point (I,J,K)
FIG. 3B
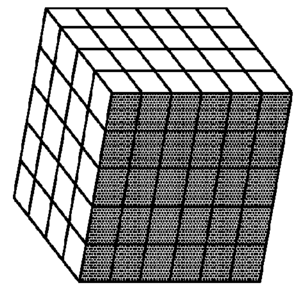
FIG. 3C

DEFORMABLE 2D-3D REGISTRATION

CROSS-REFERENCE TO RELATED APPLICATIONS

This application claims the benefit of Provisional Application No. 60/957,016 filed on Aug. 21, 2007 in the United States Patent and Trademark Office, the contents of which are herein incorporated by reference in its entirety.

BACKGROUND OF THE INVENTION

1. Technical Field

The present disclosure relates to image processing, and more particularly to a system and method for deformable 2D-3D registration.

2. Description of Related Art

During treatment of a lesion, the lesion may be is irradiated with high-energy beams produced by a linear accelerator. Treatment techniques such as 3D conformal radiation therapy and intensity modulated radiation therapy provide very accurate radiation to the lesion, while sparing healthy tissue. Efficacy of radiation treatment planning (RTP) depends on the patient setup at each daily fraction. The problem is to reproduce the patient position at the time of acquiring the planning CT scans for each fraction of the treatment process. Discrepancies between the planned and delivered treatment positions significantly degrade the therapeutic ratio.

Rigid body transformation is used to compute a correct patient setup. The drawback of such approaches is that the rigidity assumption on the imaged object is not valid for most of the patient cases, mainly due to respiratory motion.

Therefore, a need exists for a deformable 2D-3D registration.

SUMMARY OF THE INVENTION

According to an embodiment of the present disclosure, a computer implemented method for deformable registration including determining a vector field from a two-dimensional matching of a simulated two-dimensional image of a volume of an object of interest and a two-dimensional image of the object of interest, providing a deformation profile comprising control points representing movement of the object of interest over time, and finding a volume deformation that maps to a state of the two-dimensional image, wherein the deformation is parameterized by the vector field and the control points of the deformation profile to update a control point configuration of the simulated two-dimensional image of the volume of the object of interest.

According to an embodiment of the present disclosure, a system for deformable two-dimensional to three-dimensional registration includes a database for storing volumetric data of an object of interest and a processor for executing instructions of a plurality of modules processing the volumetric data. The modules include a volume deformation module generating a Digitally Reconstructed Radiograph (DRR) of the image from a deformed three-dimensional volume of the object of interest, a two-dimensional matching module for performing a non-rigid registration in two-dimensions between the DDR and an actual two-dimensional image of the object of interest and generating a two-dimensional vector field, and a two-dimensional to three-dimensional back projection module, connected to the two-dimensional matching module for receiving the two-dimensional vector field, mapping from the two-dimensional vector field as a control point grid to the deformed three-dimensional volume as a three-dimensional grid with respect to a perspective distortion.

BRIEF DESCRIPTION OF THE DRAWINGS

Preferred embodiments of the present invention will be described below in more detail, with reference to the accompanying drawings:

FIGS. 2A-B are exemplary ray castings according to an embodiment of the present disclosure; and FIGS. 3A-C shows an exemplary 2D control point lookup texture according to an embodiment of the present disclosure;

DETAILED DESCRIPTION OF PREFERRED EMBODIMENTS

According to an embodiment of the present disclosure, using 2D-3D registration, a body transformation is extracted between coordinate systems of X-ray and volumetric images, e.g., CT images. The registration may be used, for example, in external beam radiation therapy, and is useful in treating cancer, where volumetric data plays a role in radiation treatment planning. A flexible framework is implemented for deformable 2D-3D registration including a learning phase incorporating 4D CT data sets and hardware accelerated free form Digitally Reconstructed Radiograph (DRR) generation, 2D motion computation, and 2D-3D back projection.

For a flexible framework for beam radiation therapy can include pre-operative 4D data and a free-form deformation based registration scheme in 2D. Implementations in software and hardware, e.g., GPU, are considered.

Figure 1:
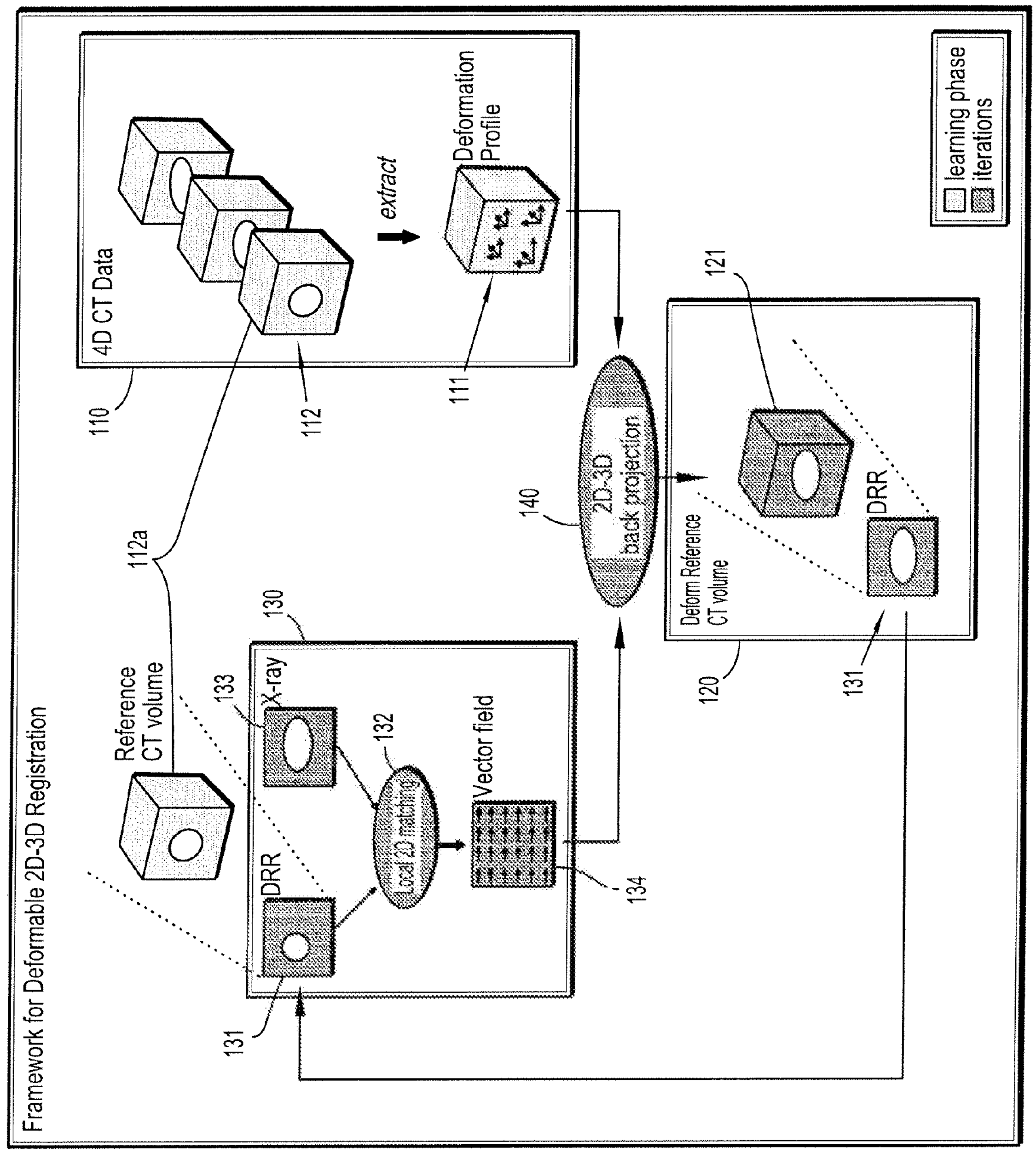
FIG. 1 is a diagram of a registration framework according to an embodiment of the present disclosure.

The flexible framework finds a CT volume deformation that maps to a patients respiration state. A free-form deformation (FFD) based framework parameterizes deformations by control points to find the optimal control point configuration. For example, referring to FIG. 1, the framework includes a movement profile generation module 110, a volume deformation module 120, a 2D matching module 130, and a based 2D-3D back projection module 140.

The movement profile generation module 110 generates deformation profiles 111 during a learning phase from 4D CT scans 112. The movement profile generation module 110 acquires the scans 112 at different stages, e.g., of respiration. A registration of the scans at different stages or time gives a displacement over time. After the registration of the scans 112 an obtained deformation profile 111 is normalized by translating 2D deformation to a control point grid configuration in 3D.

The 2D matching module 130 performs volume deformation, wherein Digitally Reconstructed Radiographs (DRRs) 131 are generated out of a deformed 3D volume 121. Here, the DRRs represent simulated 2D data generated from 3D reference data **112*a*. The reference data used to generate the DRR is taken from the 4D data 110**.

The 2D matching module 130 performs a non-rigid registration step 132 performed in 2D to match an image 133, e.g., an X-ray image, to the DDR 131 resulting in a vector field 134.

The 2D-3D back projection module 140 maps a 2D control point grid 134 to the 3D grid 111 with respect to perspective distortion to generate a simulated 3D deformation 121.

The volume deformation module 120 can implement any deformation methods, for example, volume deformation using inverse-ray-deformation (see FIGS. 2A-B), GPU assisted free-form volume deformation techniques, coarse 3D Bezier deformation, etc.

According to an embodiment of the present disclosure, the framework may be implemented together with an application working with regular control points, e.g., the DDR 131. For example, to achieve a deformation that can be used for 2D-3D deformation, the deformation performed by the volume deformation module 120 may use a spline interpolation with a small memory footprint and a GPU ray casting volume renderer can be used based on a stream model. GPU ray casting is combined with the paradigm of bended rays as shown in FIGS. 2A-B. FIG. 2A shows ray casting in a deformed volume. FIG. 2B shows deformable volume ray casting using inverse ray deformation. FIG. 2B allows for the generation of deformed images by bending rays in the opposite direction of the actual deformation, without the creation of intermediate deformed volumes.

The deformation is governed by a 3D lattice of control points (see FIG. 3C showing a cube 302 which symbolizes the 3D data set), dividing the volume into sub-cubes, each of a size $\delta_x$, $\delta_y$, $\delta_z$, provided in a separate input texture, organized as illustrated in FIGS. 3A-C. The organization of control points in a texture member is shown in FIG. 3A. A translation of control points describing the cube 302 is determined from points in FIG. 3B which specify how much a corresponding point is deformed in FIG. 3C. The sampling of the volume and the computation of ray deformation can be done in a single fragment shader with no additional memory. To increase an accuracy of the deformation, the displacement of each volume element (voxel) can be determined using 3D cubic B-splines.

An organization of 2D control point lookup texture is illustrated in FIGS. 3A-C. Each texture element stores a control point translation XYZ in its RGB channels (see FIG. 3A), starting with control points at position z=0 (a,b,c) 301.

The volume deformation method, or other method working with the regular control points, outputs a 2D image. The 2D matching module 130 matches and maps a 2D image to a 3D volume (see FIGS. 4-5), wherein the DRR serves as a moving template image and is registered to a fixed reference image (live X-ray), e.g., 402, following a free-form deformation scheme. The registration is formulated as an optimization of an energy functional aiming to minimize the distance between the two images. Such a minimization may be determined as compared to a threshold, e.g., a change in the distance between the two images for a current iteration is less than a threshold. For integration into a registration framework, this method is ported to a graphics processor and observed large performance speed-up. Using back-projection masks, the vector lengths of the obtained 2D force field can be applied to the normalized movement profile.

Figure 4:
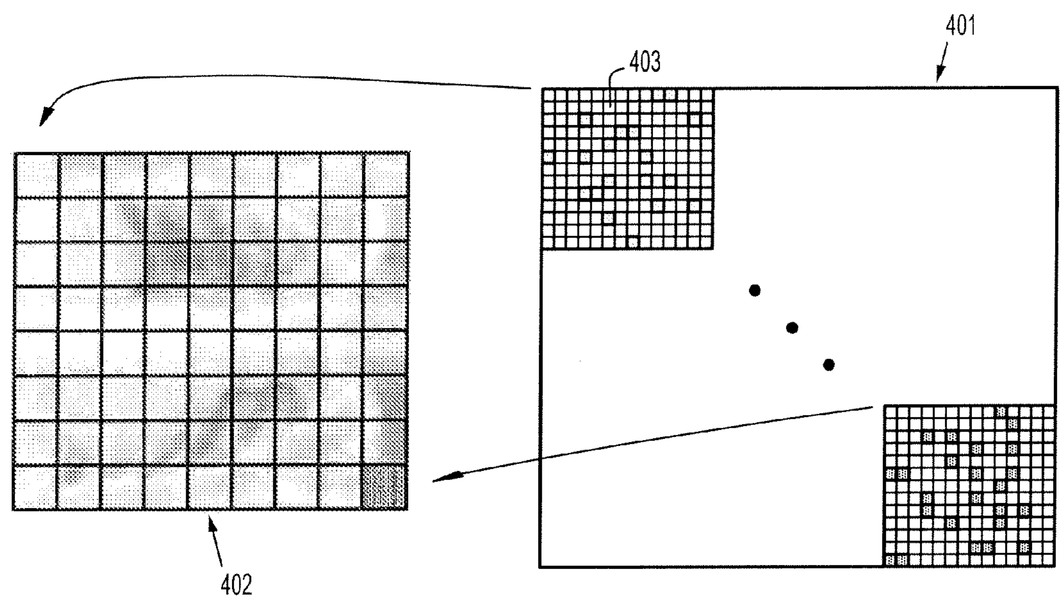
FIG. 4 shows an exemplary implementation of a back projection mask according to an embodiment of the present disclosure.

Referring to the 2D-3D back-projection 140 as illustrated in FIG. 4; a mapping from a 2D control point grid 401 to a 3D grid with respect to perspective distortion is computed each time the perspective of the X-ray device changes. Generating back-projection masks 402 allows for the detection of all control points of the free-form volume deformation that determine the appearance of blocks in a final 2D image. For each block in 2D a mask 402 of a size identical to a control point texture 401 is obtained as described with reference to FIGS. 3A-C. In each mask 402 all control points not affecting a particular block (403) are disabled by containing zero values (FIG. 5).

Figure 5:
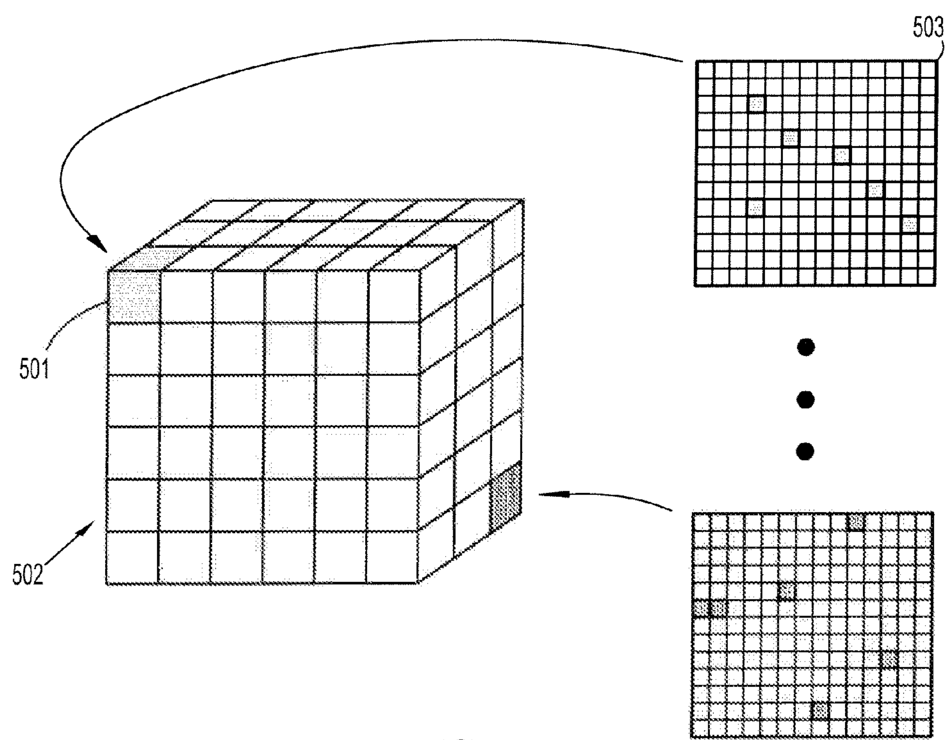
FIG. 5 shows an exemplary implementation of N control point masks for N sub-cubes according to an embodiment of the present disclosure.

For generating the back-projection masks, e.g., 402, with given volume dimensions and a number of control points, a static control point mask for each sub-cube can be computed during an initialization step (FIG. 5).

All sub-cubes, e.g., 501, of the 3D grid 502 that affect each block in 2D are determined in the same fashion as the determination of ray entry points and directions in the volume bounding box for GPU ray casting. To find out which volume sub-cubes correspond to which 2D block, e.g., 503, the method starts at a block and traverses along the ray direction in a given step size S, e.g., $S=\min(\delta_x, \delta_y, \delta_z)$. Initially, the front faces F of the volume bounding box are rendered and the resulting image is used to determine sub-cubes bordering on the bounding box current front faces. The bounding box back faces B are rendered in a separate texture to obtain ray directions. The ray directions $D=F-B$ and step size S are used to obtain all remaining sub-cubes that affect the current block. To obtain the back-projection masks of a particular block, the pre-computed control point masks (e.g., 503 of FIG. 5) of the sub-cubes that have been determined to affect the block are summed.

Figure 6:
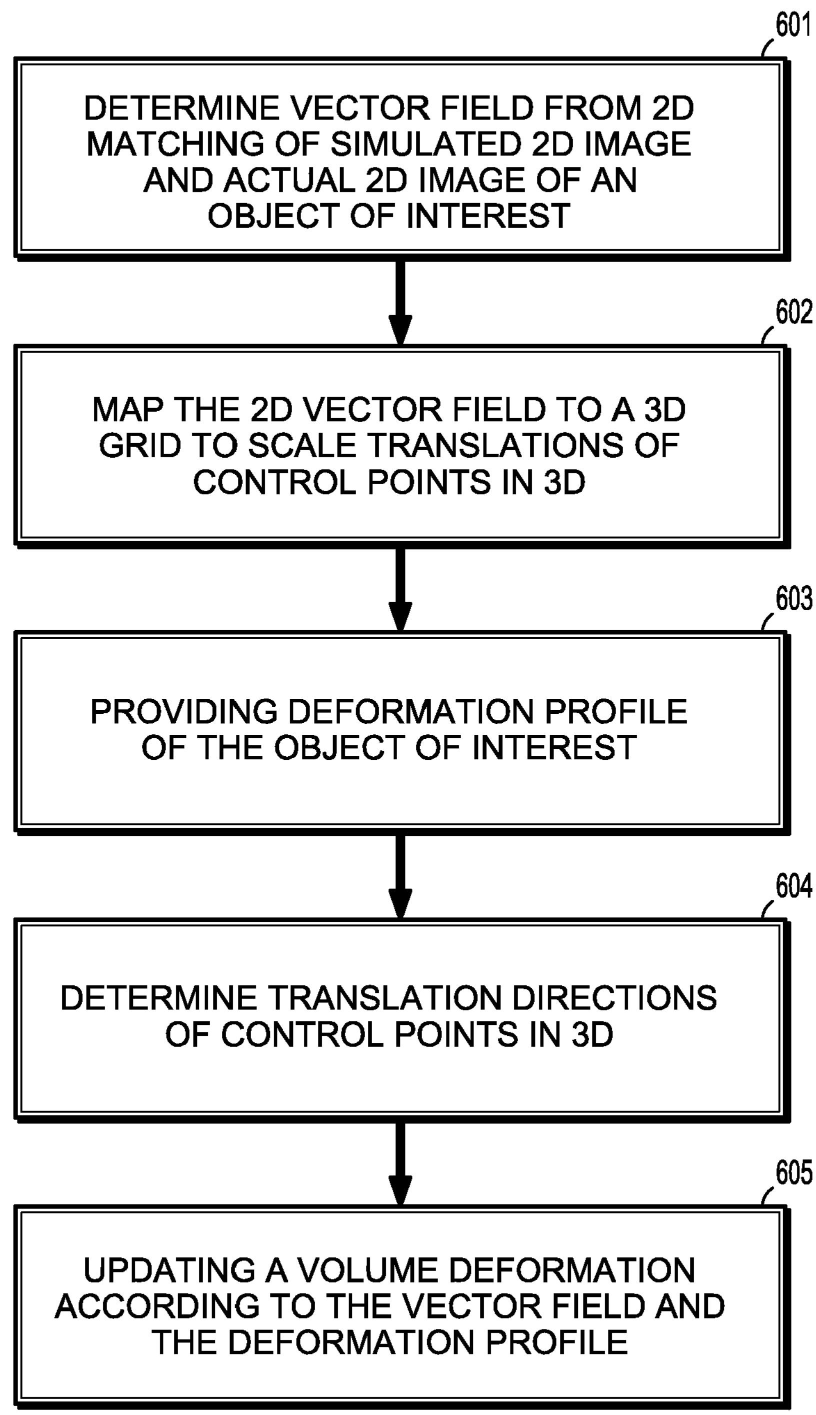
FIG. 6 shows an exemplary flow diagram according to an embodiment of the present disclosure.

Referring to FIG. 6, a method for deformable registration includes determining a vector field from a two-dimensional matching of a simulated two-dimensional image of a volume of an object of interest and a two-dimensional image of the object of interest at block 601, providing a deformation profile comprising control points representing movement of the object of interest over time at block 602, and finding a volume deformation that maps to a state of the two-dimensional image, wherein the deformation is parameterized by the vector field and the control points of the deformation profile to update a control point configuration of the simulated two-dimensional image of the volume of the object of interest at block 603. The vector field maps differences between the simulated two-dimensional image of the volume of the object of interest and the two-dimensional image of the object of interest. Finding the volume deformation includes a two-dimensional to three-dimensional back projection mapping the vector field to the deformation profile with respect to perspective distortion, and generating a simulated three-dimensional deformation.

It is to be understood that the present disclosure may be implemented in various forms of hardware, software, firmware, special purpose processors, or a combination thereof. In one embodiment, an application program is tangibly embodied on a program storage device. The application program may be uploaded to; and executed by, a machine comprising any suitable architecture.

Figure 7:
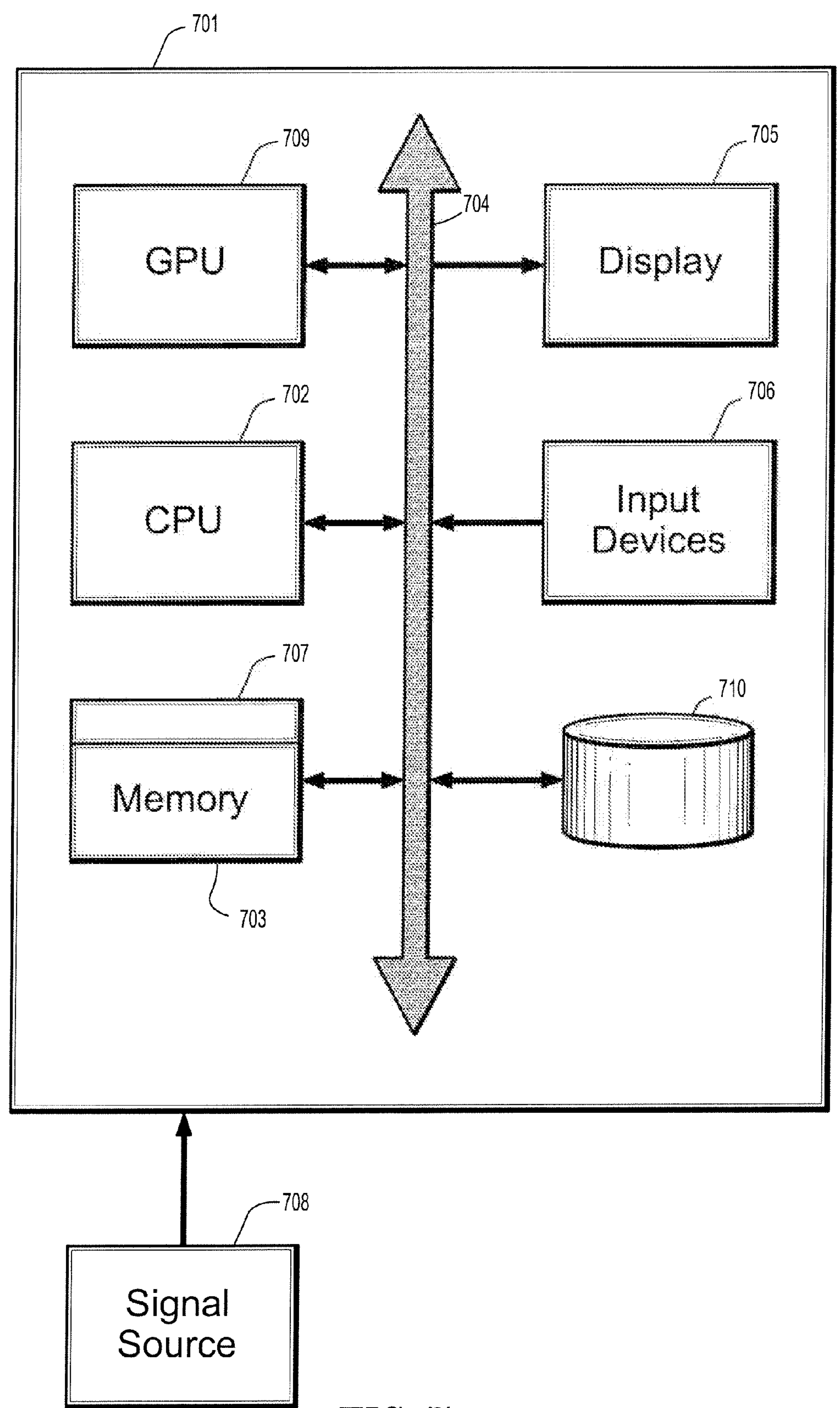
FIG. 7 is a diagram of an exemplary computer system for deformable 2D-3D registration according to an embodiment of the present disclosure.

Referring to FIG. 7, according to an embodiment of the present disclosure, a computer system 701 for deformable 2D-3D registration can comprise, inter alia, a central processing unit (CPU) 702, a memory 703 and an input/output (I/O) interface 704. The computer system 701 is generally coupled through the I/O interface 704 to a display 705 and various input devices 106 such as a mouse and keyboard. The support circuits can include circuits such as cache, power supplies, clock circuits, and a communications bus. The memory 703 can include random access memory (RAM), read only memory (ROM), disk drive, tape drive, etc., or a combination thereof. Embodiments of the present disclosure can be implemented as a routine 707 that is stored in memory 703 and executed by the CPU 702 to process the signal from the signal source 708. The computer system 701 further includes a graphics processing unit (GPU) 709 for processing graphics instructions, e.g., for processing the signal source 708 comprising image data. As such, the computer system 701 is a general purpose computer system that becomes a specific purpose computer system when executing the routine 707. The computer system 701 may further include a database 710 for storing volumetric data, etc.

The computer platform 701 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings provided herein, one of ordinary skill in the related art will be able to contemplate these and similar implementations or configurations of the present disclosure.

Having described embodiments for deformable 2D-3D registration, it is noted that modifications and variations can be made by persons skilled in the art in light of the above teachings. It is therefore to be understood that changes may be made in embodiments of the present disclosure that are within the scope and spirit thereof.

What is claimed is:

1. A computer implemented method for deformable registration comprising:

determining a vector field from a two-dimensional matching of a simulated two-dimensional image of a volume of an object of interest and a two-dimensional image of the object of interest;

providing a deformation profile comprising control points representing movement of the object of interest over time; and finding a volume deformation that maps to a state of the two-dimensional image, wherein the deformation is parameterized by the vector field and the control points of the deformation profile to update a control point configuration of the simulated two-dimensional image of the volume of the object of interest.

2. The computer implemented method of claim 1, wherein the vector field maps differences between the simulated two-dimensional image of the volume of the object of interest and the two-dimensional image of the object of interest.

3. The computer implemented method of claim 1, wherein finding the volume deformation comprises:

a two-dimensional to three-dimensional back projection mapping the vector field to the deformation profile with respect to perspective distortion; and generating a simulated three-dimensional deformation.

4. The computer implemented method of claim 3, further comprising a deformation for generating the simulated two-dimensional image of the volume of the object of interest from the simulated three-dimensional deformation.

5. A non-transitory computer readable medium embodying instructions executable by a processor to perform a method for deformable registration comprising:

determining a vector field from a two-dimensional matching of a simulated two-dimensional image of a volume of an object of interest and a two-dimensional image of the object of interest;

providing a deformation profile comprising control points representing movement of the object of interest over time; and finding a volume deformation that maps to a state of the two-dimensional image, wherein the deformation is parameterized by the vector field and the control points of the deformation profile to update a control point configuration of the simulated two-dimensional image of the volume of the object of interest.

6. The computer readable medium of claim 5, wherein the vector field maps differences between the simulated two-dimensional image of the volume of the object of interest and the two-dimensional image of the object of interest.

7. The computer readable medium of claim 5, wherein finding the volume deformation comprises:

a two-dimensional to three-dimensional back projection mapping the vector field to the deformation profile with respect to perspective distortion; and generating a simulated three-dimensional deformation.

8. The computer readable medium of claim 7, further comprising a deformation for generating the simulated two-dimensional image of the volume of the object of interest from the simulated three-dimensional deformation.

9. A method for deformable registration comprising:

capturing a volumetric data set representing a patent by a first imaging modality;

capturing a two-dimensional image representing the patient by a second imaging modality;

determining a vector field from a two-dimensional matching of a simulated two-dimensional image of the volumetric data set and the two-dimensional image;

providing a deformation profile comprising control points representing movement of the patient over time; and finding a volume deformation that maps to a state of the two-dimensional image, wherein the deformation is parameterized by the vector field and the control points of the deformation profile to update a control point configuration of the simulated two-dimensional image of the volumetric data set, and wherein the simulated two-dimensional image updated by the control point configuration is displayed.

10. The computer implemented method of claim 9, wherein the vector field maps differences between the simulated two-dimensional image of the volumetric data set and the two-dimensional image.

11. The computer implemented method of claim 9, wherein finding the volume deformation comprises:

a two-dimensional to three-dimensional back projection mapping the vector field to the deformation profile with respect to perspective distortion; and generating a simulated three-dimensional deformation.

12. The computer implemented method of claim 11, further comprising a deformation for generating the simulated two-dimensional image of the volumetric data set from the simulated three-dimensional deformation.

* * * * *